US009164104B2

(12) United States Patent
Ridker

(10) Patent No.: US 9,164,104 B2
(45) Date of Patent: Oct. 20, 2015

(54) RELEVANCE OF ACHIEVED LEVELS OF MARKERS OF SYSTEMIC INFLAMMATION FOLLOWING TREATMENT

(75) Inventor: Paul M. Ridker, Chestnut Hill, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 348 days.

(21) Appl. No.: 11/244,716

(22) Filed: Oct. 6, 2005

(65) Prior Publication Data

US 2006/0115903 A1 Jun. 1, 2006
US 2007/0292960 A9 Dec. 20, 2007

Related U.S. Application Data

(60) Provisional application No. 60/616,467, filed on Oct. 6, 2004.

(51) Int. Cl.
G01N 33/68 (2006.01)
G01N 33/92 (2006.01)
G01N 37/00 (2006.01)

(52) U.S. Cl.
CPC ........ *G01N 33/6893* (2013.01); *G01N 33/6863* (2013.01); *G01N 33/92* (2013.01); *G01N 2333/4737* (2013.01); *G01N 2800/32* (2013.01)

(58) Field of Classification Search
None
See application file for complete search history.

(56) References Cited

U.S. PATENT DOCUMENTS 6,040,147 A 3/2000 Ridker et al.
7,030,152 B1 4/2006 Ridker et al.

FOREIGN PATENT DOCUMENTS

EP 1003501 B1 3/2005
WO WO 98/43630 A1 10/1998

OTHER PUBLICATIONS

Ridker et al. 'Connecting the role of C-rective protein and stains in cardiovascular disease.' Clin. Cardiol. 26(Suppl. III):III-39-III-44, 2003.*
Wald et al. 'A strategy to reduce cardiovascular disease by more than 80%.' BMJ. 326:1419-1424, 2003. Numbered pp. 1-6.*
Ridker et al. 'Clinical Application of C-Reactive Protein for Cardiovascular Disease Detection and Prevention.' Circulation 107:363-369, 2003.*
Mega et al., "Cholesterol, C-reactive protein, and cererbrovascular events following intensive and moderate statin therapy", J. Thromb. Thrombolysis (2006), 22:71-76.
Riesen, W., et al. "Short-term effects of atorvastatin on C-reactive protein", European Heart Journal 23, pp. 794-799 (2002).
Horne, B., et al. "Statin Therapy, Lipid Level, C-Reactive Protein and the Survival of patients With Angiographically Severe Coronary Artery Disease", Journal of the American College of Cardiology, vol. 36, No. 6, pp. 1774-1780 (2000).
Kent, S., et al. "Usefulness of Lowering Low-Density Lipoprotein Cholesterol to <70 mg/dl and Usefulness of C-Reactive Protein in Patient Selection", The American Journal of Cardiology, vol. 92, pp. 1224-1227 (2003).
Ridker, P., et al. "Long-term Effects of Pravastatin on Plasma Concentration of C-reactive Protein", Circulation vol. 100, pp. 230-235, (1999).
Strandberg, T., et al. "Effect of statins on C-reactive protein in patients with coronary artery disease", The Lancet, vol. 353, pp. 118-119 (1999).
Li, J., et al. "Rapid Effects of Simvastatin on Lipid Profile and C-Reactive Protein in Patients with Hypercholesterolemia", Clin. Cardiol. 26, pp. 472-476 (2003).
Balk, E., et al. "Effects of Statins on Nonlipid Serum Markers Associated with Cardiovascular Disease", Annals of Internal Medicine, vol. 139, No. 8, pp. 670-682 & E-683-E-687, (2003).
Albert et al., Effect of statin therapy on C-reactive protein levels: the pravastatin inflammation/CRP evaluation (PRINCE): a randomized trial and cohort study. JAMA. Jul. 4, 2001;286(1):64-70.
Blake et al., Potential cost-effectiveness of C-reactive protein screening followed by targeted statin therapy for the primary prevention of cardiovascular disease among patients without overt hyperlipidemia. Am J Med. Apr. 15, 2003;114(6):485-94.
Ridker et al., Comparison of C-reactive protein and low-density lipoprotein cholesterol levels in the prediction of first cardiovascular events. N Engl J Med. Nov. 14, 2002;347(20):1557-65.
Ridker et al., Rosuvastatin in the primary prevention of cardiovascular disease among patients with low levels of low-density lipoprotein cholesterol and elevated high-sensitivity C-reactive protein: rationale and design of the JUPITER trial. Circulation. Nov. 11, 2002;108(19):2292-7.
Rifai et al., Inflammatory markers and coronary heart disease. Curr Opin Lipidol. Aug. 2002;13(4):383-9.
Supplementary European Search Report from European Patent Application 05803871.2-2404: mailed Nov. 14, 2008.
Ridker, P.M.: "High-Sensitivity C-Reactive Protein, inflammation, and cardiovascular risk:; From concept to clinical practice to clinical benefit" American Heart Journal, vol. 148, No. 1, Jul. 2004 pp. S19-S26.
Ridker P.M. et al.: "Measurement of C-reactive protein for the targeting of statin therapy in the primary prevention of acute coronary events" The New England Journal of Medicine, vol. 344, No. 26, Jun. 28, 2001, pp. 1959-1965.

(Continued)

*Primary Examiner* — Daniel E Kolker
*Assistant Examiner* — James Rogers
(74) *Attorney, Agent, or Firm* — Wolf, Greenfield & Sacks, P.C.

(57) ABSTRACT

The invention involves, inter alia, the use of markers of systemic inflammation to determine whether or not an individual undergoing treatment with a cardiovascular agent to reduce the risk of a future cardiovascular event will benefit from continued treatment with the cardiovascular agent. Further, this invention describes the use of markers of systemic inflammation to evaluate the efficacy of treatment and to assist physicians in deciding on the course of a treatment in an individual at risk of future cardiovascular events.

28 Claims, 4 Drawing Sheets

(56) References Cited

OTHER PUBLICATIONS

Ridker, P.M., et al.: "C-Reactive protein levels and outcomes after statin therapy" The New England Journal of Medicine, vol. 352, No. 1, Jan. 6, 2005, pp. 20-28.

Strandberg Timo E. et al.: "Associations between change in C-reactive protein and serum lipids during statin treatment" Annals of Medicine, Finnish Medical Society Duodecim, Helsinki, FI, vol. 32, No. 8, Nov. 1, 2000, pp. 579-583.

Cupples et al., Description of the Framingham Heart Study data for genetic analysis workshop 13. BMC Genet. 2003;4(Suppl 1):S2.

Dangas et al., Pravastatin therapy in hyperlipidemia: effects on thrombus formation and the systemic hemostatic profile. J Am Coll Cardiol. Apr. 1999;33(5):1294-304.

Milne et al., Framingham Heart Study risk equation predicts first cardiovascular event rates in New Zealanders at the population level. N Z Med J. Nov. 7, 2003;116(1185):U662.

Ridker et al., Rosuvastatin to prevent vascular events in men and women with elevated C-reactive protein. N Engl J Med. Nov. 20, 2008;359(21):2195-207. Epub Nov. 9, 2008.

Ridker et al., Reduction in C-reactive protein and LDL cholesterol and cardiovascular event rates after initiation of rosuvastatin: a prospective study of the JUPITER trial. Lancet. Apr. 4, 2009;373(9670):1175-82. Epub Mar. 28, 2009.

Wilson et al., NHLBI's Framingham CHD Risk Predictive Score Sheets. Estimating Coronary Heart Disease (CHD) Risk Using Framingham Heart Study Prediction Score Sheets. 2 pages. Retrieved online on Oct. 1, 2004 at http://www.nhlbi.nih.gov/about/framingham/riskabs.htm.

Braunwald, Creating controversy where none exists: the important role of C-reactive protein in the CARE, AFCAPS/TexCAPS, Prove It, Reversal, A to Z, JUPITER, Heart Protection, and ASCOT trials. Eur Heart J. Sep. 6, 2011. [Epub ahead of print].

Morrow et al., Clinical relevance of C-reactive protein during follow-up of patients with acute coronary syndromes in the Aggrastat-to-Zocor Trial. Circulation. Jul. 25, 2006;114(4):281-8. Epub Jul. 17, 2006.

Nissen et al., Reversal of Atherosclerosis with Aggressive Lipid Lowering (REVERSAL) Investigators. Statin therapy, LDL cholesterol, C-reactive protein, and coronary artery disease. N Engl J Med. Jan. 6, 2005;352(1):29-38.

Hao et al., Effects of fibrates on C-reactive protein concentrations: a meta-analysis of randomized controlled trials. Clin Chem Lab Med. Nov. 18, 2011;50(2):391-7. doi: 10.1515/CCLM.2011.772.

Pearson et al., Pooled analyses of effects on C-reactive protein and low density lipoprotein cholesterol in placebo-controlled trials of ezetimibe monotherapy or ezetimibe added to baseline statin therapy. Am J Cardiol. Feb. 1, 2009;103(3):369-74. doi: 10.1016/j.amjcard.2008.09.090. Epub Oct. 30, 2008.

P. M. Ridker, "Should statin therapy be considered for patients with elevated C-reactive protein? The need for a definitive clinical trial"; *European Heart Journal* (2001) 22, 2135-2137.

Ridker et al., HDL cholesterol and residual risk of first cardiovascular events after treatment with potent statin therapy: an analysis from the JUPITER trial. Lancet 2010, vol. 376, pp. 333-339.

\* cited by examiner

RELEVANCE OF ACHIEVED LEVELS OF MARKERS OF SYSTEMIC INFLAMMATION FOLLOWING TREATMENT

RELATED APPLICATION

This application claims priority under 35 U.S.C. §119(e) from U.S. provisional application Ser. No. 60/616,467 filed Oct. 6, 2004.

FIELD OF THE INVENTION

This invention is directed, in part, to the use of markers of systemic inflammation to evaluate therapy.

BACKGROUND OF THE INVENTION

Despite significant advances in diagnosis and therapy, cardiovascular events remain a major common cause of morbidity and mortality. Thus, prevention of cardiovascular events such as myocardial infarction and stroke is an area of major public health importance.

Screening tests for several risk factors for future cardiovascular events have been described and are in clinical use in the detection of human subjects at high risk. Such screening tests include, for example, cholesterol, low density lipoprotein cholesterol (LDLC), and, more recently, C-reactive protein (CRP).

Human subjects with risk factors for cardiovascular event(s) are prescribed therapies to reduce the risk of a future cardiovascular event. For example, human subjects with abnormally high cholesterol and/or LDLC levels are frequently prescribed a class of drugs called statins to reduce cholesterol levels to reduce the risk of a future cardiovascular event. However, the beneficial effects of such agents in human subjects vary in magnitude among different human subjects. The cause for this variation in response to therapy among human subjects is not clearly known yet.

Elevated levels of CRP had been described among human subjects with acute ischemia or myocardial infarction, and predict episodes of recurrent ischemia among those hospitalized with unstable angina. Elevated levels of CRP also have been associated with risk of myocardial infarction among human subjects, such as those with symptomatic angina pectoris. Subsequently, elevated levels of CRP were determined to be predictive of future cardiovascular events in human subjects otherwise healthy. The predictive capacity of CRP was also determined to be independent of the predictive capacity of lipids such as cholesterol. Notwithstanding that CRP and lipids are independent predictors, it has been discovered that lipid-lowering statin therapy of human subjects lowers not only cholesterol but also lowers the level of CRP.

Whether lowering CRP to a target level, however, leads to a lowering of the risk of future cardiovascular event is unknown. In other words, it is unknown whether a statin therapy would achieve its full benefit if it only lowers cholesterol levels or whether a full benefit is only achieved by lowering CRP levels as well. A recent study by Kent et al. (Am J Cardiol 2003; 92:1227-1230) showed that the likelihood of carotid intima-media thickness (CMIT) regression (a measure of vascular atherosclerotic disease) in human subjects was unrelated to levels of CRP when the LDLC levels was below 70 mg/dL or above 100 mg/dL. Kent et al. found no relation between the change in CMIT and either the baseline CRP or the change in CRP. To date, there are no studies that teach or suggest the use of CRP levels to guide therapy.

At this time only a few tests are available to determine whether certain therapies with cardiovascular agents, such as statins, are effective or are expected to be more or less beneficial in reducing future cardiovascular event(s). Thus, there is a need for improved tests and approaches to evaluate therapy in human subjects.

SUMMARY OF THE INVENTION

This invention is based on the surprising finding that human subjects undergoing therapy to reduce the risk of a future cardiovascular event who achieved lower on therapy levels of a marker(s) of systemic inflammation had a lower rate of recurrence of cardiovascular events. The invention is directed to monitoring the level of a marker of systemic inflammation in a human subject undergoing therapy to reduce the risk of a future cardiovascular event, in order to determine whether the human subject will benefit from continued therapy or would benefit from a change in therapy. The invention is also directed to monitoring the level of a marker of systemic inflammation in a human subject undergoing therapy to reduce the risk of a future cardiovascular event, in order to evaluate the efficacy of the therapy and/or to assist in deciding on the course of therapy.

According to one aspect of the invention, a method for diagnosing a human subject is provided. The method involves obtaining a level of a marker of systemic inflammation in a human subject undergoing therapy with a statin to reduce the risk of a future cardiovascular event. The method also involves obtaining a level of LDLC in the human subject. The level of the marker is compared to a predetermined value corresponding to a control level of the marker (e.g., in an apparently healthy population). A determination of whether the level of the marker is above a predetermined level is indicative of whether the human subject would benefit from continued therapy with the statin or would benefit from a change in therapy with the statin, when the level of LDLC is below 70 mg/dL or is above 100 mg/dL. In some embodiments, obtaining a level of the marker and obtaining a level of the LDLC are repeated so as to monitor the human subject's levels of the marker and LDLC over time. In some embodiments, the human subject may have been undergoing the therapy for at least one month. In some embodiments, the human subject may have been undergoing the therapy for at least two months.

A change in therapy with the statin refers to an increase in the dose of the statin, a switch from one statin to another statin, a switch from one statin to a non-statin anti-lipemic agent, the addition of another non-statin anti-lipemic agent to the statin therapeutic regimen, or a combination thereof.

According to another aspect of the invention, a method for evaluating the efficacy of a therapy for reducing the risk of a future cardiovascular disorder is provided. The method involves obtaining a level of a marker of systemic inflammation in a human subject undergoing therapy with a statin to reduce the risk of a future cardiovascular event. The method also involves obtaining a level of LDLC in the human subject. The level of the marker is compared to a predetermined value corresponding to a control level of the marker (e.g., in an apparently healthy population). A determination of whether the level of the marker is above a predetermined level is indicative of whether the therapy is efficacious, when the level of LDLC obtained is below 70 mg/dL or above 100 mg/dL. In some embodiments, obtaining a level of the marker and obtaining a level of the LDLC are repeated so as to monitor the human subject's levels of the marker and LDLC over time. In some embodiments, the human subject may have been undergoing the therapy for at least one month. In some embodiments, the human subject may have been undergoing the therapy for at least two months.

According to still another aspect of the invention, a method for diagnosing a patient is provided. The method involves obtaining a level of a marker of systemic inflammation in a human subject undergoing therapy with a therapeutic agent other than a statin to reduce the risk of a future cardiovascular event. The level of the marker is compared to a predetermined value corresponding to a control level of the marker (e.g., in an apparently healthy population). A determination of whether the level of the marker is above a predetermined level is indicative of whether the patient would benefit from continued therapy with the agent or would benefit from a change in therapy with the agent. In some embodiments, obtaining a level of the marker is repeated so as to monitor the human subject's level of the marker over time. In some embodiments of this aspect of the invention, the method further comprises measuring a level of a lipid in the individual, said level of lipid being further indicative of whether the patient would benefit from continued therapy with the agent or would benefit from a change in therapy with the agent.

According to another aspect of the invention, a method for evaluating the efficacy of a therapy with a therapeutic agent other than a statin for reducing the risk of a future cardiovascular event is provided. The method involves obtaining a level of a marker of systemic inflammation in a human subject undergoing the therapy to reduce the risk of a future cardiovascular event. The level of the marker is compared to a predetermined value corresponding to a control level of the marker (e.g., in an apparently healthy population). A determination of whether the level of the marker is above a predetermined level is indicative of whether the therapy is efficacious. In some embodiments, obtaining a level of the marker is repeated so as to monitor the human subject's level of the marker over time. In some embodiments of this aspect of the invention, the method further comprises measuring a level of a lipid in the individual, said level of lipid being further indicative of whether the patient would benefit from continued therapy with the agent or would benefit from a change in therapy with the agent.

According to yet another aspect of the invention method for deciding on the course of a therapy in a human subject is provided. The method involves obtaining a level of a marker of systemic inflammation in a human subject undergoing a therapy to reduce the risk of a future cardiovascular event. The level of the marker is compared to a predetermined value corresponding to a control level of the marker (e.g., in an apparently healthy population). Whether the level of the marker obtained is above a predetermined level is determined and the course of the therapy is decided based on such determination. In some embodiments, obtaining a level of the marker is repeated so as to monitor the human subject's level of the marker over time. In some embodiments of this aspect of the invention, the method further comprises measuring a level of a lipid in the individual, wherein deciding on the course of the therapy is also based upon the lipid level measured in the human subject.

According to still another aspect of the invention, a method for treating a human subject with an elevated level of marker of systemic inflammation is provided. The method involves treating the human subject with a first therapy for reducing the risk of a cardiovascular event. A level of the marker in the human subject is obtained. The level of the marker is compared to a predetermined value corresponding to a control level of the marker (e.g., in an apparently healthy population). If the predetermined level of the marker is not reached, the human subject is treated with a second therapy for reducing the risk of a cardiovascular event and the level of the marker is measured and compared to the predetermined level of the marker until the predetermined level of the marker is reached.

Examples of markers of systemic inflammation that may be used in this invention include: C-reactive protein (CRP), soluble intercellular adhesion molecule (sICAM-1), ICAM 3, BL-CAM, LFA-2, VCAM-1, NCAM, PECAM, fibrinogen, serum amyloid A (SAA), lipoprotein associated phospholipase A2 (LpPlA2), sCD40 ligand, myeloperoxidase, Interleukin-6 (IL-6), and Interleukin-8 (IL-8).

In some embodiments, the preferred marker of systemic inflammation is CRP. In some of those embodiments, the predetermined value of CRP is about 2 mg/L or lower. In other embodiments, the predetermined value is about 1.75 mg/L or lower. In still other embodiments, the predetermined value is about 1 mg/L or lower.

Examples of lipids that may be used in measurements described herein include: cholesterol, LDLC, very low density lipoprotein cholesterol (VLDLC), high density lipoprotein cholesterol (HDLC), and triglycerides. In important embodiments, the lipid is LDLC.

DETAILED DESCRIPTION OF THE INVENTION

Figure 2:
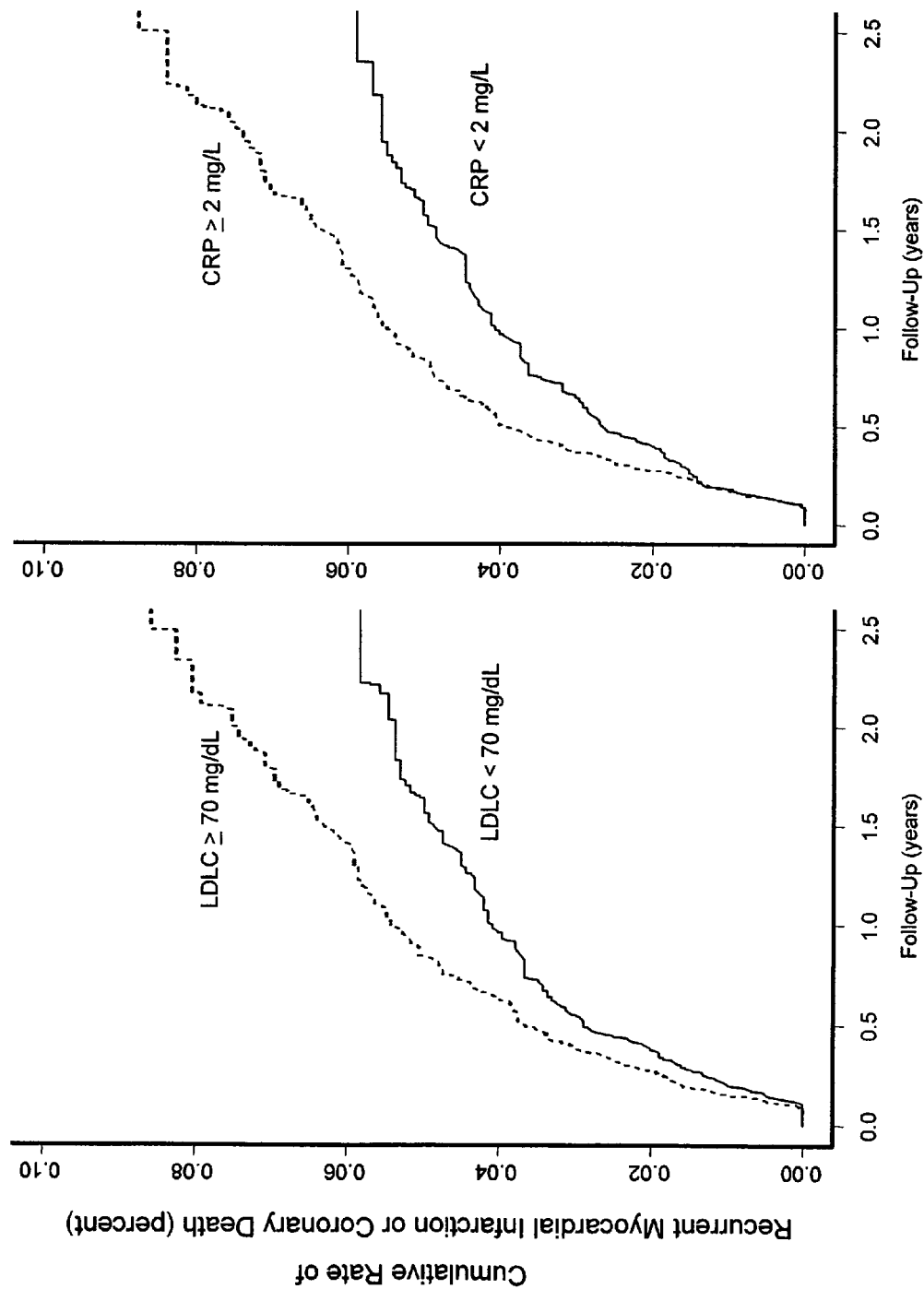
FIG. 2 is a graph of the cumulative incidence of recurrent myocardial infarction or coronary death according to achieved levels of LDLC above or below the study median value of 70 mg/dL (left) and according to achieved levels of CRP above or below the study median of 2 mg/L (right).
Figure 3:
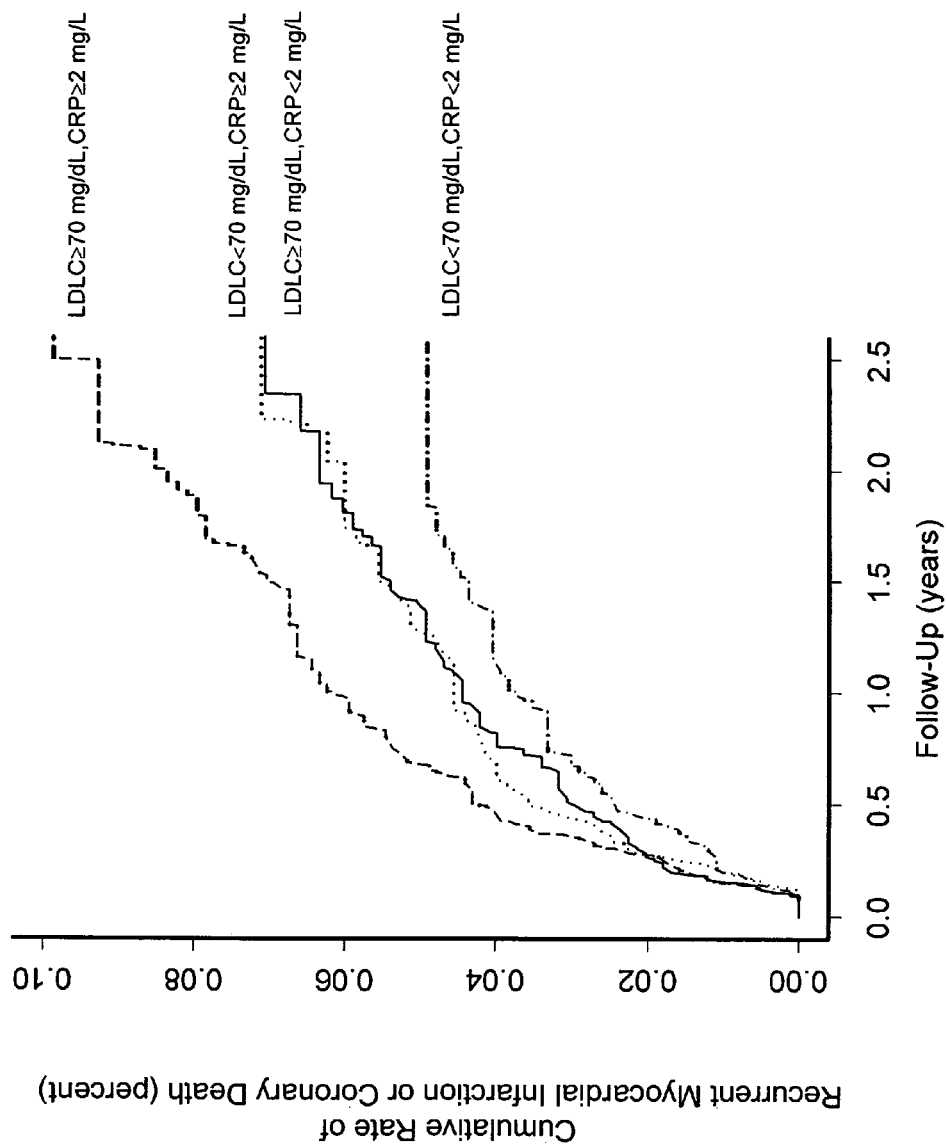
FIG. 3 is a graph of the cumulative incidence of recurrent myocardial infarction or coronary death according to achieved levels of LDLC and achieved levels of CRP.

This invention is directed to the measurement of markers of systemic inflammation to guide therapies in order to improve outcomes in human subjects. In a surprising aspect of the invention, it has been discovered that on therapy levels of markers of systemic inflammation have predictive value for the risk of future cardiovascular events. The on therapy levels of markers of systemic inflammation are additive to prior art predictors. This is illustrated in FIG. 2 and in FIG. 3, wherein the data of the present invention show the rate of recurrence of adverse cardiovascular events in human subjects, taking into account LDLC levels and CRP levels. FIG. 2 shows the rate of recurrence of cardiovascular events associated with on therapy levels of either LDLC or CRP. FIG. 3 shows the rate of recurrence of cardiovascular events associated with both LDLC levels and CRP levels. As is abundantly clear, the rate of recurrence of cardiovascular events associated with both LDLC levels and CRP levels is clearly additive.

Human subjects who would benefit from this invention are human subjects who are undergoing therapy to reduce the risk of a future cardiovascular event (i.e., a human subject "on therapy"). A human subject on therapy is a human subject who already has been diagnosed and is in the course of treatment with a therapy for reducing the risk of a future cardiovascular event. The therapy can be any of the therapeutic agents referred to below. The therapy also can be non-drug treatments such as diet and/or exercise. In important embodiments, the therapy is one which lowers levels of CRP. In a particularly important embodiment, the therapy is a therapy with a statin. The human subject most likely to benefit from this invention is a human subject on therapy and who has a CRP level above 1 mg/L.

In some embodiments, the human subject already has had a primary (first) cardiovascular event, such as, for example, a myocardial infarct or has had an angioplasty. A human subject who has had a primary cardiovascular event is at an elevated risk of a secondary (second) cardiovascular event. In some embodiments, the human subject has not had a primary cardiovascular event, but is at an elevated risk of having a cardiovascular event because the human subject has one or more risk factors to have a cardiovascular event. Examples of risk factors for a primary cardiovascular event include: hyperlipidemia, obesity, diabetes mellitus, hypertension, pre-hypertension, elevated level(s) of a marker of systemic inflammation, age, a family history of cardiovascular events, and cigarette smoking. The degree of risk of a cardiovascular event depends on the multitude and the severity or the magnitude of the risk factors that the human subject has. Risk charts and prediction algorithms are available for assessing the risk of cardiovascular events in a human subject based on the presence and severity of risk factors. One such example is the Framingham Heart Study risk prediction score. The human subject is at an elevated risk of having a cardiovascular event if the subject's 10-year calculated Framingham Heart Study risk score is greater than 5%, 6%, 7%, 8%, 9%, 10%, 11%, 12%, 13%, 14%, 15%, 16%, 17%, 18%, 19%, or 20%.

Another method for assessing the risk of a cardiovascular event in a human subject is a global risk score that incorporates a measurement of a level of a marker of systemic inflammation, such as CRP, into the Framingham Heart Study risk prediction score. Other methods of assessing the risk of a cardiovascular event in a human subject include coronary calcium scanning, cardiac magnetic resonance imaging, and/or magnetic resonance angiography.

In still other embodiments, the subject has had a primary cardiovascular event and has one or more other risk factors. In one important embodiment, the human subject is on statin therapy to reduce lipid levels. In another important embodiment, the human subject has healthy lipid levels (i.e., the human subject is not hyperlipidemic).

"Cardiovascular event," as used herein, include acute coronary syndrome, myocardial infarction, myocardial ischemia, chronic stable angina pectoris, unstable angina pectoris, angioplasty, stroke, transient ischemic attack, claudication(s), or vascular occlusion(s).

Hyperlipidemia is hypercholesterolemia and/or hypertriglyceridemia. Hypercholesterolemic human subjects and hypertriglyceridemic human subjects are associated with increased incidence of cardiovascular events. A hypercholesterolemic human subject is one who fits the current criteria established for a hypercholesterolemic human subject. A hypertriglyceridemic human subject is one who fits the current criteria established for a hypertriglyceridemic subject. A hypercholesterolemic subject has an LDL level of >160 mg/dL, or an LDL level >130 mg/dL and at least two risk factors selected from the group consisting of: male gender, family history of premature coronary heart disease, cigarette smoking, hypertension, low HDL (<35 mg/dL), diabetes mellitus, hyperinsulinemia, abdominal obesity, high lipoprotein, and personal history of a cardiovascular event. A hypertriglyceridemic human subject has a triglyceride (TG) level of ≥250 mg/dL.

Hypertension is defined as a systolic blood pressure >140 mm Hg, and/or a diastolic pressure >90 mm Hg or both. Pre-hypertension is defined as systolic blood pressure between 115 and 140 mm Hg, and/or a diastolic pressure between 80 and 90 mm Hg.

Obesity is a state of excess adipose tissue mass. Although not a direct measure of adiposity, the most widely used method to gauge obesity is the body mass index (BMI), which is equal to weight/height$^2$ (in kg/m$^2$) (See, e.g., Harrison's Principles of Experimental Medicine, 15th Edition, McGraw-Hill, Inc., N.Y.—hereinafter "Harrison's"). Based on data of substantial morbidity, a BMI of 30 is most commonly used as a threshold for obesity in both men and women. A BMI between 25 and 30 should be viewed as medically significant and worthy of therapeutic intervention, especially in the presence of risk factors that are influenced by adiposity, such as hypertension and glucose intolerance. Although often viewed as equivalent to increased body weight, this need not be the case. Lean but very muscular individuals may be overweight by arbitrary standards without having increased adiposity. Other approaches to quantifying obesity include anthropometry (skin-fold thickness), densitometry (underwater weighing), computed tomography (CT) or magnetic resonance imaging (MRI), and/or electrical impedance.

Diabetes mellitus is established in a human subject with a fasting plasma glucose level of 125 mg/dL or higher.

An elevated level(s) of a marker of systemic inflammation is a level that is above the average for a healthy human subject population (i.e., human subjects who have no signs and symptoms of disease). When the marker of systemic inflammation is CRP, a CRP level of ≥1 is considered an elevated level.

Therapies for reducing the risk of a future cardiovascular event include but are not limited to diet and/or exercise and/or therapies with: anti-lipemic agents, anti-inflammatory agents, anti-thrombotic agents, fibrinolytic agents, anti-platelet agents, direct thrombin inhibitors, glycoprotein IIb/IIIa receptor inhibitors, agents that bind to cellular adhesion molecules and inhibit the ability of white blood cells to attach to such molecules (e.g. anti-cellular adhesion molecule antibodies), alpha-adrenergic blockers, beta-adrenergic blockers, cyclooxygenase-2 inhibitors, angiotensin system inhibitor, anti-arrhythmics, calcium channel blockers, diuretics, inotropic agents, vasodilators, vasopressors, thiazolidinediones, cannabinoid-1 receptor blockers and/or any combinations thereof.

Anti-lipemic agents are agents that reduce total cholesterol, reduce LDLC, reduce triglycerides, and/or increase HDLC. Anti-lipemic agents include statins and non-statin anti-lipemic agents, and/or combinations thereof. Statins are a class of medications that have been shown to be effective in lowering human total cholesterol, LDLC and triglyceride levels. Statins act at the step of cholesterol synthesis. By reducing the amount of cholesterol synthesized by the cell, through inhibition of the HMG-CoA reductase gene, statins initiate a cycle of events that culminates in the increase of LDLC uptake by liver cells. As LDLC uptake is increased, total cholesterol and LDLC levels in the blood decrease. Lower blood levels of both factors are associated with lower risk of atherosclerosis and heart disease, and the statins are widely used to reduce atherosclerotic morbidity and mortality.

Examples of statins include, but are not limited to, simvastatin (Zocor), lovastatin (Mevacor), pravastatin (Pravachol), fluvastatin (Lescol), atorvastatin (Lipitor), cerivastatin (Baycol), rosuvastatin (Crestor), pitivastatin and numerous others described in U.S. Pat. Nos. 4,444,784, 4,231,938, 4,346,227, 4,739,073, 5,273,995, 5,622,985, 5,135,935, 5,356,896, 4,920,109, 5,286,895, 5,262,435, 5,260,332, 5,317,031, 5,283,256, 5,256,689, 5,182,298, 5,369,125, 5,302,604, 5,166,171, 5,202,327, 5,276,021, 5,196,440, 5,091,386, 5,091,378, 4,904,646, 5,385,932, 5,250,435, 5,132,312, 5,130,306, 5,116,870, 5,112,857, 5,102,911, 5,098,931, 5,081,136; 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860, 4,940,800, 4,940,727, 4,939,143, 4,929,620, 4,923,861, 4,906,657, 4,906,624 and 4,897,402.

Examples of statins already approved for use in humans include atorvastatin, cerivastatin, fluvastatin, pravastatin, simvastatin and rosuvastatin. The reader is referred to the following references for further information on HMG-CoA reductase inhibitors: Drugs and Therapy Perspectives (May 12, 1997), 9: 1-6; Chong (1997) Pharmacotherapy 17: 1157-1177; Kellick (1997) Formulary 32: 352; Kathawala (1991) Medicinal Research Reviews, 11: 121-146; Jahng (1995) Drugs of the Future 20: 387-404, and Current Opinion in Lipidology, (1997), 8, 362-368. Another statin drug of note is compound 3a (S-4522) in Watanabe (1997) Bioorganic and Medicinal Chemistry 5: 437-444.

Non-statin anti-lipemic agents include but are not limited to fibric acid derivatives (fibrates), bile acid sequestrants or resins, nicotinic acid agents, cholesterol absorption inhibitors, acyl-coenzyme A: cholesterol acyl transferase (ACAT) inhibitors, cholesteryl ester transfer protein (CETP) inhibitors, LDL receptor antagonists, farnesoid X receptor (FXR) antagonists, sterol regulatory binding protein cleavage activating protein (SCAP) activators, microsomal triglyceride transfer protein (MTP) inhibitors, squalene synthase inhibitors, and peroxisome proliferation activated receptor (PPAR) agonists.

Examples of fibric acid derivatives include but are not limited to gemfibrozil (Lopid), fenofibrate (Tricor), clofibrate (Atromid) and bezafibrate.

Examples of bile acid sequestrants or resins include but are not limited to colesevelam (WelChol), cholestyramine (Questran or Prevalite) and colestipol (Colestid), DMD-504, GT-102279, HBS-107 and S-8921.

Examples of nicotinic acid agents include but are not limited to niacin and probucol.

Examples of cholesterol absorption inhibitors include but are not limited to ezetimibe (Zetia).

Examples of ACAT inhibitors include but are not limited to Avasimibe, CI-976 (Parke Davis), CP-113818 (Pfizer), PD-138142-15 (Parke Davis), F1394, and numerous others described in U.S. Pat. Nos. 6,204,278, 6,165,984, 6,127,403, 6,063,806, 6,040,339, 5,880,147, 5,621,010, 5,597,835, 5,576,335, 5,321,031, 5,238,935, 5,180,717, 5,149,709, and 5,124,337.

Examples of CETP inhibitors include but are not limited to Torcetrapib, CP-529414, CETi-1, JTT-705, and numerous others described in U.S. Pat. Nos. 6,727,277, 6,723,753, 6,723,752, 6,710,089, 6,699,898, 6,696,472, 6,696,435, 6,683,099, 6,677,382, 6,677,380, 6,677,379, 6,677,375, 6,677,353, 6,677,341, 6,605,624, 6,586,448, 6,521,607, 6,482,862, 6,479,552, 6,476,075, 6,476,057, 6,462,092, 6,458,852, 6,458,851, 6,458,850, 6,458,849, 6,458,803, 6,455,519, 6,451,830, 6,451,823, 6,448,295, 5,512,548.

One example of an FXR antagonist is Guggulsterone. One example of a SCAP activator is GW532 (GlaxoSmithKline).

Examples of MTP inhibitors include but are not limited to Implitapide and R-103757.

Examples of squalene synthase inhibitors include but are not limited to zaragozic acids.

Examples of PPAR agonists include but are not limited to GW-409544, GW-501516, and LY-510929.

Anti-inflammatory agents include Alclofenac, Alclometasone Dipropionate, Algestone Acetonide, Alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Deflazacort, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lornoxicam, Loteprednol Etabonate, Meclofenamate Sodium, Meclofenamic Acid, Meclorisone Dibutyrate, Mefenamic Acid, Mesalamine, Meseclazone, Methylprednisolone Suleptanate, Morniflumate, Nabumetone, Naproxen, Naproxen Sodium, Naproxol, Nimazone, Olsalazine Sodium, Orgotein, Orpanoxin, Oxaprozin, Oxyphenbutazone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Salycilates, Sanguinarium Chloride, Seclazone, Sermetacin, Sudoxicam, Sulindac, Suprofen, Talmetacin, Talniflumate, Talosalate, Tebufelone, Tenidap, Tenidap Sodium, Tenoxicam, Tesicam, Tesimide, Tetrydamine, Tiopinac, Tixocortol Pivalate, Tolmetin, Tolmetin Sodium, Triclonide, Triflumidate, Zidometacin, Glucocorticoids, Zomepirac Sodium.

Anti-thrombotic agents and/or fibrinolytic agents include tissue plasminogen activator (e.g., Activase, Alteplase)(catalyzes the conversion of inactive plasminogen to plasmin. This may occur via interactions of prekallikrein, kininogens, Factors XII, XIIIa, plasminogen proactivator, and tissue plasminogen activator TPA) Streptokinase, Urokinase, Anisoylated Plasminogen-Streptokinase Activator Complex, Pro-Urokinase, (Pro-UK), rTPA (alteplase or activase; r denotes recombinant), rPro-UK, Abbokinase, Eminase, Sreptase Anagrelide Hydrochloride, Bivalirudin, Dalteparin Sodium, Danaparoid Sodium, Dazoxiben Hydrochloride, Efegatran Sulfate, Enoxaparin Sodium, Ifetroban, Ifetroban Sodium, Tinzaparin Sodium, retaplase, Trifenagrel, Warfarin, Dextrans, aminocaproic acid (Amicar), and tranexamic acid (Amstat).

Anti-platelet agents include Clopridogrel, Sulfinpyrazone, Aspirin, Dipyridamole, Clofibrate, Pyridinol Carbamate, PGE, Glucagon, Antiserotonin drugs, Caffeine, Theophyllin Pentoxifyllin, Ticlopidine, Anagrelide.

Direct thrombin inhibitors include hirudin, hirugen, hirulog, agatroban, PPACK, thrombin aptamers.

Glycoprotein IIb/IIIa receptor Inhibitors are both antibodies and non-antibodies, and include but are not limited to ReoPro (abcixamab), lamifiban, tirofiban.

Agents that bind to cellular adhesion molecules and inhibit the ability of white blood cells to attach to such molecules include polypeptide agents. Such polypeptides include polyclonal and monoclonal antibodies, prepared according to conventional methodology. Such antibodies already are known in the art and include anti-ICAM 1 antibodies as well as other such antibodies. Significantly, as is well-known in the art, only a small portion of an antibody molecule, the paratrope, is involved in the binding of the antibody to its epitope (see, in general, Clark, W. R. (1986) *The Experimental Foundations of Modern Immunology*, Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-know in the art, there are complementarity determining regions (CDRs), which directly interact with the epitope of the antigen, and framework regions (Frs), which maintain the tertiary structure of the paratope (see, in general, Clar, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also encompasses for $F(ab')_2$, Fab, Fv and Fd fragments; chimeric antibodies in which the Fc and/or Fr and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or nonhuman sequences. The present invention also includes so-called single chain antibodies.

Thus, the invention encompasses polypeptides of numerous size and type that bind specifically to cellular adhesion molecules. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Examples of alpha-adrenergic blockers include: doxazocin, prazocin, tamsulosin, and tarazosin.

Beta-adrenergic receptor blocking agents are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide. The above-identified compounds can be used as isomeric mixtures, or in their respective levorotating or dextrorotating form.

Cyclooxygenase-2 (COX-2) is a recently identified new form of a cyclooxygenase. Cyclooxygenase is an enzyme complex present in most tissues that produces various prostaglandins and thromboxanes from arachidonic acid. Nonsteroidal, antiinflammatory drugs exert most of their antiinflammatory, analgesic and antipyretic activity and inhibit hormone-induced uterine contractions and certain types of cancer growth through inhibition of the cyclooxygenase (also known as prostaglandin G/H synthase and/or prostaglandin-endoperoxide synthase). Initially, only one form of cyclooxygenase was known, the "constitutive enzyme" or cyclooxygenase-1 (COX-1). It was originally identified in bovine seminal vesicles.

Cyclooxygenase-2 (COX-2) has been cloned, sequenced and characterized initially from chicken, murine and human sources (See, e.g., U.S. Pat. No. 5,543,297, issued Aug. 6, 1996 to Cromlish, et al., and assigned to Merck Frosst Canada, Inc., Kirkland, Calif., entitled: "Human cyclooxygenase-2 cDNA and assays for evaluating cyclooxygenase-2 activity"). This enzyme is distinct from the COX-1. COX-2, is rapidly and readily inducible by a number of agents including mitogens, endotoxin, hormones, cytokines and growth factors. As prostaglandins have both physiological and pathological roles, it is believed that the constitutive enzyme, COX- 1, is responsible, in large part, for endogenous basal release of prostaglandins and hence is important in their physiological functions such as the maintenance of gastrointestinal integrity and renal blood flow. By contrast, it is believed that the inducible form, COX-2, is mainly responsible for the pathological effects of prostaglandins where rapid induction of the enzyme would occur in response to such agents as inflammatory agents, hormones, growth factors, and cytokines. Therefore, it is believed that a selective inhibitor of COX-2 has similar antiinflammatory, antipyretic and analgesic properties to a conventional non-steroidal antiinflammatory drug, and in addition inhibits hormone-induced uterine contractions and also has potential anti-cancer effects, but with reduced side effects. In particular, such COX-2 inhibitors are believed to have a reduced potential for gastrointestinal toxicity, a reduced potential for renal side effects, a reduced effect on bleeding times and possibly a decreased potential to induce asthma attacks in aspirin-sensitive asthmatic subjects, and are therefore useful according to the present invention.

A number of selective COX-2 inhibitors are known in the art. These include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 "N-benzyl indol-3-yl butanoic acid derivatives as cyclooxygenase inhibitors"; U.S. Pat. No. 5,677,318 "Diphenyl-1,2-3-thiadiazoles as anti-inflammatory agents"; U.S. Pat. No. 5,691,374 "Diaryl-5-oxygenated-2-(5H) -furanones as COX-2 inhibitors"; U.S. Pat. No. 5,698,584 "3,4-diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

An angiotensin system inhibitor is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin I and angiotensin II are synthesized by the enzymatic renin-angiotensin pathway. The synthetic process is initiated when the enzyme renin acts on angiotensinogen, a pseudoglobulin in blood plasma, to produce the decapeptide angiotensin I. Angiotensin I is converted by angiotensin converting enzyme (ACE) to angiotensin II (angiotensin-[1-8] octapeptide). The latter is an active pressor substance which has been implicated as a causative agent in several forms of hypertension in various mammalian species, e.g., humans.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists. In a preferred embodiment of the invention, the renin-angiotensin system inhibitors are renin inhibitors, ACE inhibitors, and angiotensin II antagonists.

Angiotensin II antagonists are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid. Stability can be enhanced by other replacements that slow degeneration in vivo. Examples of angiotensin II receptor antagonists include but are not limited to: Candesartan (Alacand), Irbesartan (Avapro), Losartan (Cozaar), Telmisartan (Micardis), and Valsartan (Diovan). Other examples of angiotensin II antagonists include: peptidic compounds (e.g., saralasin, [(Sar$^1$)(Val$^5$)(Ala$^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., *J. Pharmacol. Exp. Ther.* 247(1), 1-7 (1988)); 4,5,6,7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No.

5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl) -L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl) methyl] 1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G.D.Searle and Company).

Angiotensin converting enzyme (ACE), is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410, 520), phosphinylalkanoyl prolines such as fosinopril (U.S. Pat. No. 4,337,201) and trandolopril.

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di and tri peptide derivatives (U.S. Pat. No. 5,106,835); amino acids and derivatives thereof (U.S. Pat. Nos. 5,104,869 and 5,095, 119); diol sulfonamides and sulfinyls (U.S. Pat. No. 5,098, 924); modified peptides (U.S. Pat. No. 5,095,006); peptidyl beta-aminoacyl aminodiol carbamates (U.S. Pat. No. 5,089, 471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063, 208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Calcium channel blockers are a chemically diverse class of compounds having important therapeutic value in the control of a variety of diseases including several cardiovascular disorders, such as hypertension, angina, and cardiac arrhythmias (Fleckenstein, *Cir. Res.* v. 52, (suppl. 1), p. 13-16 (1983); Fleckenstein, *Experimental Facts and Therapeutic Prospects*, John Wiley, New York (1983); McCall, D., *Curr Pract Cardiol*, v. 10, p. 1-11 (1985)). Calcium channel blockers are a heterogenous group of drugs that prevent or slow the entry of calcium into cells by regulating cellular calcium channels. (Remington, *The Science and Practice of Pharmacy*, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, amrinone, amlodipine, bencyclane, felodipine, fendiline, flunarizine, isradipine, nicardipine, nimodipine, perhexilene, gallopamil, tiapamil and tiapamil analogues (such as 1993RO-11-2933), phenytoin, barbiturates, and the peptides dynorphin, omega-conotoxin, and omega-agatoxin, and the like and/or pharmaceutically acceptable salts thereof.

Diuretics include but are not limited to: carbonic anhydrase inhibitors, loop diuretics, potassium-sparing diuretics, thiazides and related diuretics.

Vasodilators include but are not limited to coronary vasodilators and peripheral vasodilators.

Vasopressors are agents that produce vasoconstriction and/or a rise in blood pressure. Vasopressors include but are not limited to: dopamine, ephedrine, epinephrine, Methoxamine HCl (Vasoxyl), phenylephrine, phenylephrine HCl (Neo-Synephrine), and Metaraminol.

Thiazolidinediones include but are not limited to: rosiglitazone (Avandia), pioglitazone (Actos), troglitazone (Rezulin). Combination therapies of thiazolidinediones and other agents such as rosiglitazone and metformin (Avandamet) are encompassed by this invention.

One example of a cannabinoid-1 receptor blocker is rimonabant.

In practicing the methods of the present invention, it is required to obtain a level of a marker of systemic inflammation in an individual. Markers of systemic inflammation are well-known to those of ordinary skill in the art. It is preferred that the markers of systemic inflammation be selected from the group consisting of CRP, cytokines, and cellular adhesion molecules. Cytokines are well-known to those of ordinary skill in the art and include human interleukins 1-17. Cellular adhesion molecules are well-known to those of ordinary skill in the art and include integrins, soluble intercellular adhesion molecule (sICAM-1), ICAM-3, BL-CAM, LFA-2, VCAM-1, NCAM, PECAM, fibrinogen, serum amyloid A (SAA), lipoprotein associated pospholipase A2 (LpPlA2), sCD40 ligand, myeloperoxidase, Interleukin-6 (IL-6) and Interleukin-8 (IL-8). One of the preferred adhesion molecule is sICAM-1.

To practice the method, a level of a marker of systemic inflammation in a human subject on therapy is obtained. This level then is compared to a predetermined value, wherein the level of the marker of systemic inflammation in comparison to the predetermined value is indicative of the likelihood that the individual will benefit from continued therapy. The individual then can be characterized in terms of the net benefit likely to be obtained from a change therapy.

The level of the marker of systemic inflammation for the individual can be obtained by any art recognized method. Typically, the level is determined by measuring the level of the marker in a body fluid, for example, blood, lymph, saliva, urine and the like. The level can be determined by ELISA, or immunoassays or other conventional techniques for determining the presence of the marker. Conventional methods include sending a sample(s) of a patient's body fluid to a commercial laboratory for measurement.

The invention also involves comparing the level of marker for the individual with a predetermined value. The predetermined value can take a variety of forms. It can be single cut-off value, such as a median or mean. It can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quartiles, the lowest quartile being individuals with the lowest risk and the highest quartile being individuals with the highest risk, or into tertiles the lowest tertile being individuals with the lowest risk and the highest tertile being individuals with the highest risk.

The predetermined value can depend upon the particular population of human subjects selected. For example, an apparently healthy population will have a different 'normal' range of markers of systemic inflammation than will as a population the human subjects of which have had a prior cardiovascular event. Accordingly, the predetermined values selected may take into account the category in which a human subject falls. Appropriate ranges and categories can be selected with no more than routine experimentation by those of ordinary skill in the art.

The preferred body fluid is blood and the preferred marker is CRP. When the marker of systemic inflammation is CRP, one preferred predetermined value is about 3 mg/L of blood (i.e., blood sample from the human subject). Another preferred predetermined value is about 2 mg/L of blood. Another preferred predetermined value is about 1.75 mg/L of blood. Another preferred predetermined value is about 1.50 mg/L of blood. Another preferred predetermined value is about 1.25 mg/L of blood. Another preferred predetermined value is about 1 mg/L of blood. When ranges are employed, one of the preferred plurality of ranges is below about 3 mg/L of blood and another of the ranges is above about 3 mg/L of blood. Another preferred plurality of ranges is below about 2 mg/L of blood and another of the ranges is above about 2 mg/L of blood. Another preferred plurality of ranges is below about 1 mg/L of blood and another of the ranges is above about 1 mg/L of blood. CRP is a predictor of risk of a cardiovascular event.

When the marker of systemic inflammation is sICAM-1, a cellular adhesion molecule, then a preferred predetermined value is about 250 ng/ml of blood.

When the marker of systemic inflammation is sCD40 ligand, a preferred predetermined value is about 5.5 ng/mL of blood. Another preferred predetermined value is about 3.2 ng/mL of blood. Another preferred predetermined value is about 2.9 ng/mL of blood.

An important predetermined value of a marker of systemic inflammation is a value that is the average for a healthy human subject population (i.e., human subjects who have no signs and symptoms of disease). The predetermined value will depend, of course, on the particular marker selected and even upon the characteristics of the patient population in which the individual lies. In characterizing risk, numerous predetermined values can be established.

Presently there are commercial sources which produce reagents for assays for CRP. These include, but are not limited to, Dade-Behring (Deerfield, Ill.), Abbott Pharmaceuticals (Abbott Park, Ill.), CalBiochem (San Diego, Calif.) and Behringwerke (Marburg, Germany). Commercial sources for inflammatory cytokine and cellular adhesion molecule measurements, include, but are not limited to, R&D Systems (Minneapolis, Minn.), Genzyme (Cambridge, Mass.) and Immunotech (Westbrook, Me.).

Agents that bind to cellular adhesion molecules and inhibit the ability of white blood cells to attach to such molecules include polypeptide agents. Such polypeptides include poly-clonal and monoclonal antibodies, prepared according to conventional methodology. Such antibodies already are known in the art and include anti-ICAM 1 antibodies as well as other such antibodies.

The invention further comprises measuring the level of a marker of systemic inflammation together with the level of a lipid such as, for example, a level of cholesterol or a level of a cholesterol fraction such as LDLC for characterizing a human subject's risk of developing a future cardiovascular event. A level of a marker of systemic inflammation in the human subject is obtained. The level of the marker is compared to a predetermined value to establish a first risk value. A level of lipid in the human subject also is obtained. The level of the lipid in the human subject is compared to a second predetermined value to establish a second risk value. The human subject's risk profile of developing the cardiovascular event then is characterized based upon the combination of the first risk value and the second risk value, wherein the combination of the first risk value and second risk value establishes a third risk value different from the first and second risk values. In some embodiments, the third risk value is greater than either of the first and second risk values. The preferred human subjects for testing, markers and predetermined values are as described above. The cardiovascular event can be any cardiovascular event such as described above.

The invention provides methods for determining whether a human subject will benefit from continued therapy or would benefit from a change in therapy. The benefit is typically a reduction in the rate of occurrence of cardiovascular events. Determining whether a human subject will benefit from continued therapy or would benefit from a change in therapy is clinically useful. One example of clinical usefulness of the methods of this invention includes identifying human subjects who are less likely or more likely to respond to a therapy. The methods of the invention are also useful in predicting or determining that a human subject would benefit from continued therapy or would benefit from a change in therapy. Another example of clinical usefulness includes aiding clinical investigators in the selection for clinical trials of human subjects with a high likelihood of obtaining a net benefit. It is expected that clinical investigators now will use the present invention for determining entry criteria for clinical trials.

A human subject who would benefit from continued therapy is a human subject whose on therapy level of the marker of systemic inflammation reaches a certain predetermined value. In some embodiments the marker of systemic inflammation is CRP. Predetermined values of CRP are described above. A human subject who would benefit from a change in therapy is a human subject whose on therapy level of the marker of systemic inflammation did not reach a certain predetermined value.

As used herein, a "change in therapy" refers to an increase or decrease in the dose of the existing therapy, a switch from one therapy to another therapy, an addition of another therapy to the existing therapy, or a combination thereof. A switch from one therapy to another may involve a switch to a therapy with a high risk profile but where the likelihood of expected benefit is increased. In some embodiments, preferred therapies are therapies that lower levels of CRP. A human subject who would benefit from a change in therapy by increasing the dose of the existing therapy is a human subject who, for example, was on the therapy but was not receiving the maximum tolerated dose or the maximum allowed dose of the therapy and whose level of the marker of systemic inflammation did not reach a certain predetermined value. In such instances the dose of the existing therapy is increased until the level of the marker of systemic inflammation reaches a certain predetermined value. In some instances, the dose of the existing therapy is increased from the existing dose to a higher dose that is not the maximum tolerated dose nor the maximum allowed dose of the therapy. In other instances, the dose is increased to the maximum tolerated or to the maximum allowed dose of the therapy. A human subject who would benefit from a change in therapy by decreasing the dose of the existing therapy is, for example, a human subject whose on therapy level of marker of inflammation reaches or can reach a certain predetermined value with a lower dose of the therapy.

A human subject who would benefit from a switch from one therapy to another therapy is, for example, a human subject who was on the maximum tolerated dose or the maximum allowed dose of the therapy and whose level of a marker of systemic inflammation did not reach a certain predetermined value. Another example is a human subject was not on the maximum tolerated or the maximum allowed dose of the therapy but was determined by a health care practitioner to more likely benefit from another therapy. Such determinations are based, for example, on the development in the human subject of unwanted side effects on the initial therapy or a lack of response to the initial therapy.

A human subject who would benefit from a change in therapy by the addition of another therapy to the existing therapy is, for example, a human subject who was on a therapy but whose level of a marker of systemic inflammation did not reach a certain predetermined value. In such instances, another therapy is added to the existing therapy. The therapy that is added to the existing therapy can have a different mechanism of action in lowering the level of the marker of systemic inflammation than the existing therapy. In some instances, a combination of the aforementioned changes in therapy may be used.

When the therapy is with a statin, a change in therapy refers to an increase in the dose of the statin, a switch from one statin to another statin, a switch from one statin to a non-statin anti-lipemic agent, the addition of another non-statin anti-lipemic agent to the statin that the human subject was on, or a combination thereof. Statins and non-statin anti-lipemic agents are described above.

The invention also provides methods for determining the efficacy of a therapy. The efficacy is typically the efficacy of the therapy in lowering the level of a marker of sytemic inflammation (e.g., lowering of CRP). This is sometimes also referred to as a positive response or a favorable response. Efficacy can be determined by a CRP blood test(s) to determine whether CRP levels are lowered as a result of therapy. In some embodiments efficacy determination is based on the efficacy of a therapy in lowering both CRP and lipid levels (e.g., cholesterol or LDLC). Tests and methods for measuring CRP and lipid levels in blood, especially serum samples, and for interpreting results of such tests are widely used in clinical practice today.

A lipid test (e.g. cholesterol) is often performed to evaluate risks for heart disease. As is known in the art, cholesterol is an important normal body constituent, used in the structure of cell membranes, synthesis of bile acids, and synthesis of steroid hormones. Since cholesterol is water insoluble, most serum cholesterol is carried by lipoproteins (chylomicrons, VLDLC, LDLC, and HDLC). Excess cholesterol in the blood has been correlated with cardiovascular events. LDL is sometimes referred to as "bad" cholesterol, because elevated levels of LDL correlate most directly with cardiovascular events such as coronary heart disease. HDL is sometimes referred to as "good" cholesterol since high levels of HDL are correlated with a reduced risk for cardiovascular events such as coronary heart disease. The term total cholesterol means "total" cholesterol i.e. VLDLC+LDLC+HDLC Preferably, CRP and cholesterol levels are measured after a patient has fasted. The cholesterol measurement is typically reported in milligrams per deciliter (mg/dL). Typically, the higher the total cholesterol, the more at risk a human subject is for a cardiovascular event. A value of total cholesterol of less than 200 mg/dL is a "desirable" level and places the human subject in a group at less risk for a cardiovascular event(s). Levels over 240 mg/dL, for example, may put a human subject at almost twice the risk of cardiovascular event such as coronary heart disease as compared to someone with a level less than 200 mg/dL.

LDLC levels are predictors of risk of cardiovascular event. Typically, the higher the LDLC, the more at risk a human subject is for cardiovascular event. Levels of LDLC over 160 mg/dL may put a human subject at higher risks of a cardiovascular event(s) as compared to someone with a level less than 160 mg/dL. Levels of LDLC over 130 mg/dL in human subject with one or more risk factors for a future cardiovascular event may put a human subject at higher risks of a cardiovascular event(s) as compared to someone with a level less than 130 mg/dL. A level of LDLC less than 100 mg/dL is desirable in a human subject who has had a prior cardiovascular event and is on therapy to reduce the risk of a future cardiovascular event and places the human subject in a group at less risk for a cardiovascular event. A level of LDLC less than 70 mg/dL is even more desirable in a such a human subject to reduce the risk of a future cardiovascular event.

The invention also provides methods for deciding on the course of a therapy in a human subject undergoing therapy to reduce the risk of a future adverse cardiovascular event. Such a course of therapy is decided on the basis of the level of a marker of systemic inflammation. Therapies for reducing the risk of future cardiovascular events are described above. In some embodiments, the human subject already has had a cardiovascular event, such as, for example, a myocardial infarct or has had an angioplasty. A human subject who has had a primary (first) cardiovascular event is at an elevated risk of a secondary (second) cardiovascular event due to the primary cardiovascular event. In some embodiments, the human subject is at an elevated risk of a cardiovascular event because the human subject has one or more risk factors to have a cardiovascular event. Examples of risk factors to have a cardiovascular event are described above. In some embodiments, the human subject who is at an elevated risk of a cardiovascular event may be an apparently healthy human subject. An apparently healthy human subject is described above.

These methods have important implications for patient treatment and also for the clinical development of new therapies. It is also expected that clinical investigators now will use the present methods for determining entry criteria for human subjects in clinical trials. Health care practitioners select therapeutic regimens for treatment based upon the expected net benefit to the human subject. The net benefit is derived from the risk to benefit ratio. The present invention permits the determination of whether a human subject will benefit from continued therapy or would benefit from a change in therapy, thereby aiding the physician in selecting a therapy.

When a therapeutic agent is administered, it is administered in an amount effective to reduce the risk of a future adverse cardiovascular event. An effective amount is a dosage of the therapeutic agent sufficient to provide a medically desirable result. The effective amount will vary with the particular condition being treated, the age and physical condition of the subject being treated, the severity of the condition, the duration of the treatment, the nature of the concurrent therapy (if any), the specific route of administration and the like factors within the knowledge and expertise of the health care practitioner. For example, an effective amount can depend upon the degree to which an individual has abnormally elevated levels of markers of systemic inflammation. It should be understood that the therapeutic agents of the invention are used to prevent cardiovascular events, that is, they are used prophylactically in human subjects at risk of developing a cardiovascular event. Thus, an effective amount is that amount which can lower the risk of, slow or perhaps prevent altogether the development of a cardiovascular event. When the therapeutic agent is one that binds to cellular adhesion molecules and inhibits the ability of white blood cells to attach to such molecules, then the agent may be used prophylactically or may be used in acute circumstances, for example, post-myocardial infarction or post-angioplasty. It will be recognized when the therapeutic agent is used in acute circumstances, it is used to prevent one or more medically undesirable results that typically flow from such adverse events. In the case of myocardial infarction, the therapeutic agent can be used to limit injury to the cardiovascular tissue which develops as a result of the myocardial infarction and in the case of restenosis, the therapeutic agent can be used in amounts effective to inhibit, prevent or slow the reoccurrence of blockage. In either case, it is an amount sufficient to inhibit the infiltration of white blood cells and transmigration of white blood cells into the damaged tissue, which white blood cells can result in further damage and/or complications relating to the injury.

Generally, doses of active compounds or agents would be from about 0.01 mg/kg per day to 1000 mg/kg per day. It is expected that doses ranging from 50-500 mg/kg will be suitable, preferably orally and in one or several administrations per day. Lower doses will result from other forms of administration, such as intravenous administration. In the event that a response in a human subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

When administered, pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The therapeutic agents may be combined, optionally, with a pharmaceutically-acceptable carrier. The term "pharmaceutically-acceptable carrier" as used herein means one or more compatible solid or liquid filler, diluents or encapsulating substances which are suitable for administration into a human subject. The term "carrier" denotes an organic or inorganic ingredient, natural or synthetic, with which the active ingredient is combined to facilitate the application. The components of the pharmaceutical compositions also are capable of being co-mingled with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the therapeutic agent, which is preferably isotonic with the blood of the subject. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular therapeutic agent selected, the severity of the condition being treated and the dosage required for therapeutic efficacy. The methods of the invention, generally speaking, may be practiced using any mode of administration that is medically acceptable, meaning any mode that produces effective levels of the active compounds or agents without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the therapeutic agent into association with a carrier which constitutes one or more accessory ingredients. In general, the compositions are prepared by uniformly and intimately bringing the therapeutic agent into association with a liquid carrier, a finely divided solid carrier, or both, and then, if necessary, shaping the product.

Compositions suitable for oral administration may be presented as discrete units, such as capsules, tablets, lozenges, each containing a predetermined amount of the therapeutic agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the therapeutic agent, increasing convenience to the subject and the health care practitioner. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and triglycerides; hydrogel release systems; sylastic systems; peptide based systems; wax coatings; compressed tablets using conventional binders and excipients; partially fused implants; and the like. Specific examples include, but are not limited to: (a) erosional systems in which the therapeutic agent is contained in a form within a matrix such as those described in U.S. Pat. Nos. 4,452,775, 4,667,014, 4,748,034 and 5,239,660 and (b) difusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for therapy of chronic conditions. Long-term release, are used herein, means that the implant is constructed and arranged to deliver therapeutic levels of the active ingredient for at least 30 days, and preferably 60 days. Long-term sustained release implants are well-known to those of ordinary skill in the art and include some of the release systems described above.

In some embodiments the invention provides novel kits or assays which are specific for, and have appropriate sensitivity with respect to, predetermined values selected on the basis of the present invention. The preferred kits, therefore, would differ from those presently commercially available, by including, for example, different cut-offs, different sensitivities at particular cut-offs as well as instructions or other printed material for characterizing risk based upon the outcome of the assay.

The invention will now be illustrated but not limited by reference to the following Example.

EXAMPLE

This study addressed the relationships between achieved LDLC levels, achieved CRP levels, and recurrent myocardial infarction or coronary death among 3,745 acute coronary syndrome patients treated with atorvastatin 80 mg or pravastatin 40 mg for 24 months.

Statin therapy lowers the risk of cardiovascular events by reducing plasma cholesterol and practice guidelines for patients with known cardiovascular disease emphasize the importance of reaching target goals for LDLC (1). However, we have shown that statin therapy results in a greater clinical benefit when levels of the inflammatory biomarker CRP are elevated (2,3) and that statins lower CRP levels in a manner largely independent of LDLC (3-6). These findings, along with basic laboratory evidence, have lead to the hypothesis that in addition to being potent lipid lowering agents, statins might also have anti-inflammatory properties that are important for prognosis and treatment. If so, then the level of CRP achieved after treatment with statin therapy might have clinical relevance in a manner analogous to that of achieved LDLC levels.

We prospectively addressed this issue among 3,745 patients with acute coronary syndrome who were randomly allocated to an intensive or moderate lipid lowering statin regimen. Specifically, on an a priori basis, we hypothesized that acute coronary syndrome patients who achieved lower CRP levels would have a better outcome in terms of recurrent myocardial infarction or coronary death than those who achieved higher CRP levels, even after controlling for levels of achieved LDLC. We also sought evidence of effect modification by choice of statin regimen.

Methods

The study population derived from the Pravastatin or Atorvastatin Evaluation and Infection Therapy-Thrombolysis in Myocardial Infarction 22 (PROVE IT-TIMI 22) study, a randomized trial performed between November 2000 and February 2004 that used a 2 by 2 factorial design to evaluate the effect of intensive (atorvastatin 80 mg/day orally) versus moderate (pravastatin 40 mg/day orally) statin therapy and of gatifloxicin versus placebo in the prevention of recurrent coronary events following acute coronary syndrome (7). In total, 4,162 patients who had been hospitalized within the preceding 10 days for acute coronary syndrome and provided written informed consent were enrolled at 349 sites in eight countries. Approximately two-thirds had acute myocardial infarction and the remainder had high-risk unstable angina. Descriptions of the study inclusion and exclusion criteria have been presented previously (8).

As part of the PROVE IT-TIMI 22 protocol, plasma samples were sought at randomization and at day 30, 4 months, and the end of study (mean 24 months). For this analysis, we defined achieved LDLC and achieved CRP levels as those values obtained at the 30 day follow-up, a period of time adequate for the effect of statin therapy to be seen for both LDLC and CRP and a time when any residual effects of ischemia on each parameter would no longer be evident. Of the total cohort, 3,745 participants (90.0 percent) were alive and free of a recurrent event at day 30 and underwent evaluation for both LDLC and CRP at that time. All laboratory measurements were made in core facilities and a validated assay for high sensitivity CRP used (Denka Seiken).

Spearman correlation coefficients were used to evaluate the relationship between achieved LDLC and achieved CRP. We then used a multi-stage process to address the impact of achieved LDLC and achieved CRP levels on rates of recurrent myocardial infarction or fatal coronary events that occurred after day 30 in the study. First, we divided the study population into increasing quartiles of achieved LDLC and achieved CRP and sought evidence that these levels were associated with increased risk of recurrent myocardial infarction or coronary death, both in age-adjusted analyses and after further adjustment for gender, smoking status (current/non-smoker), diabetes, body mass index ($kg/m^2$), and history of hypertension. Second, we divided the study population at the approximate median achieved LDLC of 70 mg/dL and addressed whether those above and below this value had differential rates of recurrent events. In a similar manner, we divided the study population at the approximate median achieved CRP of 2.0 mg/L and addressed whether those above or below this value had differential rates of recurrent events. To address the relative impact of achieved CRP across LDLC strata, we repeated this process after dividing the study cohort into four groups on the basis of achieved LDLC levels and achieved CRP levels above or below the respective values of 70 mg/dL and 2.0 mg/L. A test for trend across groups was performed assigning a score of 0 to those with low levels of both, a score of 1 to the two intermediate groups, and a score of 2 to those with high levels of both. Similar analyses were performed after stratification of the study group according to atorvastatin or pravastatin allocation. Estimates of hazard ratios were obtained using Cox proportional-hazards models. All main analyses were pre-specified in the PROVE IT-TIMI 22 protocol (8). All P values are two-tailed, all confidence intervals computed at the 95 percent level, and all analyses adjusted for gatifloxicin allocation.

Results

Mean age of the 3,745 participants at study entry was 58 years and 22 percent were women. 49 percent had a history of hypertension, 17 percent were diabetic, and 36 percent were current smokers.

Figure 1:
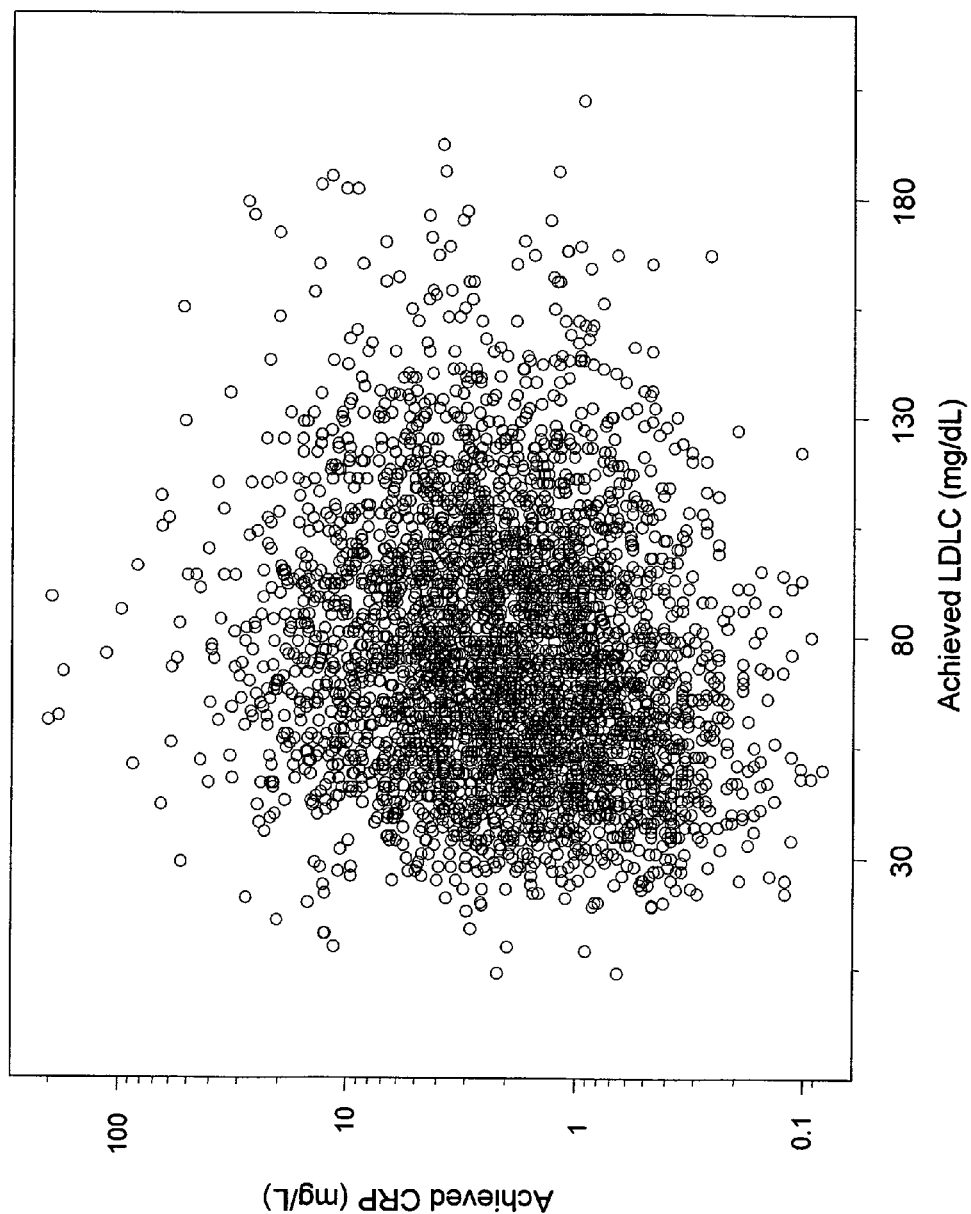
FIG. 1 is a plot of the relationship of achieved low density lipoprotein cholesterol (LDLC) (mg/dL) and achieved CRP levels (mg/L) after 30 days of statin therapy. Overall, less than 3 percent of the variation in achieved CRP was explained by variation in achieved LDLC (r=0.016, P=0.001).

While both LDLC and CRP were reduced by statin therapy at 30 days, the correlation between achieved LDLC and achieved CRP was small (r=0.16, P<0.001) such that <3 percent of the variance in achieved CRP was explained by achieved LDLC (FIG. 1). This minimal level of correlation was also observed in the subgroup of patients who subsequently suffered recurrent coronary events (r=0.18, P=0.004).

There was a linear relationship between achieved LDLC levels following statin therapy and the risk of recurrent myocardial infarction or coronary death. Fully adjusted relative risks for those with the lowest (referent) to highest quartiles of achieved LDLC were 1.0, 1.1, 1.2, and 1.7 respectively (P comparing highest to lowest quartile=0.006) (Table 1). However, despite almost complete independence of achieved CRP and achieved LDLC, there was also a linear relationship between achieved CRP levels following statin therapy and the risk of recurrent myocardial infarction or coronary death such that fully adjusted relative risks for those with the lowest (referent) to highest quartiles of achieved CRP were 1.0, 1.5, 1.3, and 1.7 (P comparing highest to lowest quartile=0.01). Additional adjustment for concomitant medications had no effect on these estimates.

TABLE 1

| | Quartile | | | |
|---|---|---|---|---|
| | 1 | 2 | 3 | 4 |
| Achieved LDLC (mg/dL) | (<54) | (54-72) | (72-94) | (>94) |
| RR (adjusted for age) | 1.0 | 1.1 | 1.3 | 1.8 |
| 95% CI | — | 0.75-1.6 | 0.92-1.9 | 1.2-2.5 |
| P | — | 0.6 | 0.1 | 0.002 |
| RR (adjusted for age, achieved CRP) | 1.0 | 1.1 | 1.3 | 1.7 |
| 95% CI | — | 0.73-1.6 | 0.87-1.8 | 1.2-2.4 |
| P | — | 0.7 | 0.2 | 0.006 |
| RR (adjusted for age, risk factors*) | 1.0 | 1.1 | 1.3 | 1.7 |
| 95% CI | — | 0.73-1.6 | 0.88-1.9 | 1.2-2.5 |
| P | — | 0.7 | 0.2 | 0.003 |
| RR (fully adjusted) | 1.0 | 1.1 | 1.2 | 1.7 |
| 95% CI | — | 0.71-1.6 | 0.84-1.8 | 1.2-2.4 |
| P | — | 0.8 | 0.3 | 0.006 |
| Achieved CRP (mg/L) | (<0.9) | (0.9-1.9) | (1.9-4.2) | (>4.2) |
| RR (adjusted for age) | 1.0 | 1.5 | 1.5 | 1.9 |
| 95% CI | — | 1.0-2.3 | 1.0-2.3 | 1.3-2.8 |
| P | — | 0.04 | 0.04 | <0.001 |
| RR (adjusted for age, achieved LDLC) | 1.0 | 1.5 | 1.4 | 1.8 |
| 95% CI | — | 0.98-2.2 | 0.97-2.1 | 1.2-2.6 |
| P | — | 0.06 | 0.07 | 0.004 |
| RR (adjusted for age, risk factors*) | 1.0 | 1.5 | 1.4 | 1.8 |
| 95% CI | — | 1.0-2.3 | 0.94-2.1 | 1.2-2.7 |
| P | — | 0.04 | 0.09 | 0.003 |
| RR (fully adjusted) | 1.0 | 1.5 | 1.3 | 1.7 |
| 95% CI | — | 0.99-2.2 | 0.89-2.0 | 1.1-2.5 |
| P | — | 0.06 | 0.15 | 0.01 |

*All models controlled for age (years). Risk factor adjusted models additionally controlled for gender, smoking status (current/non-smoker), diabetes (yes/no), history of hypertension (yes/no), body mass index (kg/m²) and random allocation to gatifloxicin. In addition to the above covariates, the fully adjusted model for achieved LDLC also adjusted for achieved CRP, while the fully adjusted model for achieved CRP also adjusted for achieved LDLC.

Age-adjusted rates of recurrent myocardial infarction or coronary death are shown in Table 2 according to achieved LDLC levels above or below 70 mg/dL, achieved CRP levels above or below 2 mg/L, and in strata combining both achieved LDLC and CRP.

TABLE 2

| Patient Group | Patients (N) | Person Years | Recurrent Events (N) | Age-adjusted Event Rate/100 person-years | |
|---|---|---|---|---|---|
| LDLC ≥ 70 mg/dL | 1985 | 3850.7 | 148 | 4.0 | P = 0.008 |
| LDLC < 70 mg/dL | 1760 | 3511.5 | 95 | 2.7 | |
| CRP ≥ 2 mg/L | 1828 | 3559.3 | 139 | 3.9 | P = 0.006 |
| CRP < 2 mg/L | 1917 | 3802.9 | 104 | 2.8 | |
| LDL ≥ 70 mg/dL, CRP ≥ 2 mg/L | 1086 | 2086.2 | 92 | 4.6 | P < 0.001 |
| LDL < 70 mg/dL, CRP ≥ 2 mg/L | 742 | 1473.0 | 47 | 3.1 | |
| LDL ≥ 70 mg/dL, CRP < 2 mg/L | 899 | 1764.5 | 56 | 3.2 | |
| LDL < 70 mg/dL, CRP < 2 mg/L | 1018 | 2038.4 | 48 | 2.4 | |
| CRP ≥ 1 mg/L | 2699 | 5250.7 | 200 | 3.8 | P < 0.001 |
| CRP < 1 mg/L | 1046 | 2111.5 | 43 | 2.1 | |
| LDL ≥ 70 mg/dL, CRP ≥ 1 mg/L | 1536 | 2952.3 | 128 | 4.5 | P < 0.001 |
| LDL < 70 mg/dL, CRP ≥ 1 mg/L | 1163 | 2298.4 | 72 | 3.1 | |
| LDL ≥ 70 mg/dL, CRP < 1 mg/L | 449 | 898.4 | 20 | 2.3 | |
| LDL < 70 mg/dL, CRP < 1 mg/L | 597 | 1213.0 | 23 | 1.9 | |

Patients who achieved LDLC levels <70 mg/dL had lower age-adjusted rates of recurrent myocardial infarction or coronary death compared to those who failed to achieve this goal (2.7 vs 4.0 events/100 person-years, P=0.008) (FIG. 2, left). However, despite minimal correlation between achieved LDLC and achieved CRP, a virtually identical difference in age-adjusted event rates was also observed for patients who achieved CRP levels <2.0 mg/L as compared to those who did not (2.8 vs 3.9 events/100 person-years, P=0.006) (FIG. 2, right).

As also shown in Table 2, those who achieved lower CRP levels had better clinical outcomes at both high and low levels of achieved LDLC. For example, among patients with achieved LDLC ≥70 mg/dL, recurrent event rates were 4.6 and 3.2 per 100 person-years respectively for those with achieved CRP levels above or below 2.0 mg/L, while for patients who achieved LDLC <70 mg/dL, recurrent event rates were 3.1 and 2.4 per 100 person-years respectively for those with achieved CRP levels above or below 2.0 mg/L. These differences are presented graphically in terms of cumulative incidence of recurrent myocardial infarction or coronary death in FIG. 3. Hazard ratios for recurrent coronary events among those in the below median LDLC/below median CRP, above median LDLC/below median CRP, below median LDLC/above median CRP, and above median LDLC/above median CRP groups were 1.0 (referent), 1.3, 1.4, and 1.9, respectively (P for trend across groups <0.001). Almost identical results were observed in analyses that eliminated patients with prior statin use.

Because study participants were randomly allocated between atorvastatin 80 mg and pravastatin 40 mg, we had the additional opportunity to address the relative impact of these two agents on CRP reduction and to address whether the main effects observed in the total cohort according to achieved LDLC and achieved CRP levels were modified by the choice of statin therapy.

Figure 4:
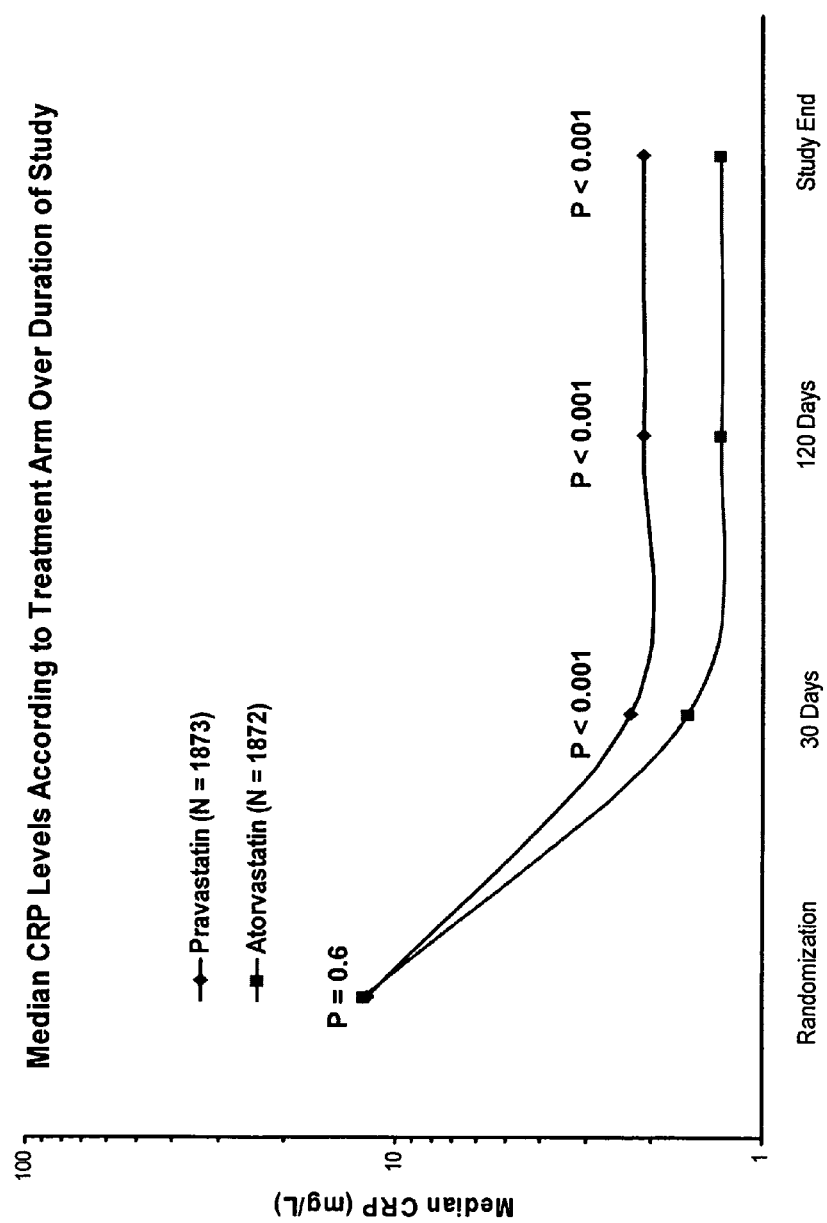
FIG. 4 is a graph of the median levels of CRP at randomization, at 30 days, at 4 months, and at end of study, according to atorvastatin 80 mg or pravastatin 40 mg allocation.

With regard to CRP, median levels were similar in the atorvastatin 80 mg and pravastatin 40 mg groups at randomization (12.2 vs 11.9 mg/L, P=0.6), but were significantly lower in the atorvastatin as compared to pravastatin groups at day 30 (1.6 vs 2.3 mg/L), 4 months (1.3 vs 2.1 g/L), and end of study (1.3 vs 2.1 mg/l) (all P-values <0.001) (FIG. 4). Despite these differences, there was substantial overlap between atorvastatin and pravastatin treated patients in terms of achieved CRP levels; 57.5 percent of those treated with atorvastatin achieved CRP levels below 2.0 at day 30 whereas the comparable proportion for pravastatin was 44.9 percent (P<0.001). With regard to LDLC, levels were identical in the atorvastatin and pravastatin groups at randomization and as expected, were significantly lower in the atorvastatin treated group at day 30, 4 months, and end of study. At day 30, 72.3 percent of those allocated to atorvastatin achieved an LDLC goal of <70 mg/dL as compared to 21.7 percent of those allocated to pravastatin (P<0.001). The magnitude of correlation between achieved LDLC and achieved CRP was small for both agents (r=0.04, P=0.07 for pravastatin; r=0.15, P=0.001 for atorvastatin).

Despite the greater ability of atorvastatin 80 mg as compared to pravastatin 40 mg to reduce LDLC and CRP below the levels of 70 mg/dL and 2.0 mg/L, there was little evidence that any specific agent led to better clinical outcomes once target levels of both LDLC and CRP were achieved. Specifically, although atorvastatin was superior to pravastatin overall in the PROVE IT-TIMI 22 trial (7), there was no observed residual effect of randomized drug allocation on clinical outcomes once achieved LDLC and achieved CRP were accounted for (fully adjusted hazard ratio for atorvastatin vs pravastatin=1.00, 95% CI 0.75 to 1.34, P=0.9). Similarly, for those who achieved LDLC levels less than 70 mg/dL on atorvastatin, recurrent event rates were 3.1 and 2.3 per 100 person-years respectively for those with achieved CRP levels greater than and less than 2.0 mg/L while the corresponding event rates for those allocated pravastatin were 3.4 and 2.5 per 100 person years (P for a difference between agents=0.7). Thus, achieving target levels of both LDLC and CRP was of substantially greater importance for subsequent event free survival than was the specific allocation to either atorvastatin or pravastatin.

On a post hoc basis we performed additional analyses to evaluate those who not only achieved an LDLC target of <70 mg/dL, but who also achieved an even lower CRP target of <1.0 mg/L. Although only 16 percent of the study population reached these very aggressive target goals, this subgroup had the very lowest age-adjusted recurrent event rate observed in any analysis (1.9 events per 100 person-years) (Table 2, bottom). 82 percent of those in this post-hoc subgroup had been allocated to atorvastatin.

As indicated above, all analyses adjusted for gatifloxicin allocation, an agent that had no significant effect on CRP levels in this population.

Discussion

These data indicate that among acute coronary syndrome patients treated with statin therapy, achieving a target level of CRP less than 2.0 mg/L is associated with significantly improved event free survival, an effect present at all levels of achieved LDLC. These data also demonstrate that the relationship between LDLC reduction and CRP reduction for individual patients is highly variable regardless of the intensity of lipid lowering regimen used, a finding consistent with prior studies of individuals without acute ischemia (3-6). In our data, less than 3 percent of the variation in achieved CRP was explained by the variation in achieved LDLC. Thus, these data suggest that strategies to aggressively lower cardiovascular risk with statin therapy may need to monitor levels of inflammation as well as cholesterol.

These data have clinical relevance for several reasons. First, while the PROVE IT-TIMI 22 study demonstrates the importance of achieving LDLC levels <70 mg/dL after acute coronary syndrome, the current analyses indicate that subsequent event free survival is also linked to achieving CRP levels <2.0 mg/L. This concept is supported by observations using intravascular ultrasound in which the magnitude of change in CRP as well as the magnitude of change in LDLC were both found to be independent predictors of plaque regression following statin therapy (9). Thus, while confirming the importance of achieving LDL levels <70 mg/dL in very high-risk patients as recently advocated (10), our observations regarding the clinical relevance of achieved CRP levels may be important for future guidelines designed to address the appropriate use of statin therapy.

Second, these data are of pathophysiologic importance as they provide evidence that reducing inflammation in general and perhaps CRP in particular may well have a role in altering the atherothrombotic process. To date, a consistent series of prospective epidemiologic studies demonstrate that CRP levels independently predict risk of first coronary events at all levels of LDLC and across a full spectrum of Framingham Risk (11-16) and that CRP levels have prognostic utility in acute coronary syndromes (17-20). However, while statin therapy has been shown to lower CRP levels in a largely LDLC independent manner (2-6, 21, 22), there has been no prior evidence linking greater CRP reduction to lowered vascular event rates. In the current analysis, more intensive statin therapy was found to achieve significantly lower LDLC and CRP levels, yet there was evidence of incremental benefit for those who achieved CRP levels <2.0 mg/L among those who did and did not reduce LDLC levels below 70 mg/L. In this regard, these data are consistent with laboratory work indicating the importance of inflammation as a determinant of plaque instability (23) as well as experimental data indicating that statins provide lipid lowering and anti-inflammatory effects (24). Our data also support ongoing efforts to find agents capable of lowering CRP as a potential novel method of vascular risk reduction.

Third, our data demonstrating the concomitant importance of both lipid reduction and CRP reduction provides insight into mechanisms by which more aggressive statin regimens augment vascular risk reduction. In the current data, those allocated to atorvastatin 80 mg were significantly more likely to achieve low levels of both LDLC and CRP than those allocated to pravastatin 40 mg, data consistent with other studies (25). Nonetheless, we found little evidence of differential outcome by drug once target levels were met suggesting that achieved LDLC and achieved CRP levels were more important in determining outcomes than specific choice of agent. The observation that treatment group was not associated with outcome after controlling for achieved LDLC and achieved CRP provides strong support for the hypothesis that more aggressive therapy when needed to achieve these targets will reduce risk. Clinical trials testing two doses of the same statin will be needed to fully evaluate this issue.

Participants in the PROVE IT-TIMI 22 trial had suffered a recent myocardial infarction or had high-risk unstable angina and thus had a clear indication for long term statin therapy. As such, we believe interpretation of our findings should not be generalized beyond secondary prevention. In primary prevention, post hoc analysis from the AFCAPS/TexCAPS trial suggest that apparently healthy individuals with elevated CRP levels but low lipid levels benefit from statin therapy (3). However, whether or not statin therapy should be used in primary prevention among individuals with elevated levels of CRP who do not have hyperlipidemia remains highly controversial and is the subject of an ongoing multinational trial (26, 27).

In summary, these secondary prevention data demonstrate improved cardiovascular event free survival among those who achieve aggressive target levels of both LDLC and CRP following statin therapy. These data also provide strong evidence supporting the hypothesis that therapies designed to reduce inflammation after acute coronary ischemia may lead to improved patient outcomes.

References

1. Expert panel on detection, evaluation, and treatment of high blood cholesterol in adults. Executive summary of the third report of the national cholesterol education program (NCEP) expert panel on detection, evaluation, and treatment of high blood cholesterol in adults (Adult Treatment Panel III). JAMA 2001; 285:2486-97.
2. Ridker P M, Rifai N, Pfeffer M A, et al. Inflammation, pravastatin, and the risk of coronary events after myocardial infarction in patients with average cholesterol levels. Cholesterol and Recurrent Events (CARE) Investigators. Circulation 1998; 98:839-44.
3. Ridker P M, Rifai N, Clearfield M, et al. Measurement of C-reactive protein for the targeting of statin therapy in the primary prevention of acute coronary events. N Engl J Med 2001; 344:1959-65.
4. Ridker P M, Rifai N, Pfeffer M A, Sacks F, Braunwald E. Long-term effects of pravastatin on plasma concentration of C-reactive protein. The Cholesterol and Recurrent Events (CARE) Investigators. Circulation 1999; 100:230-5.
5. Albert M A, Danielson E, Rifai N, Ridker P M. Effect of statin therapy on C-reactive protein levels: the pravastatin inflammation/CRP evaluation (PRINCE): a randomized trial and cohort study. JAMA 2001; 286:64-70.
6. Ridker P M, Rifai N, Lowenthal S P. Rapid reduction in C-reactive protein with cerivastatin among 785 patients with primary hypercholesterolemia. Circulation 2001; 103:1191-3.
7. Cannon C P, Braunwald E, McCabe C H, et al for the PROVE IT-TIMI 22 Investigators. Comparison of intensive and moderate lipid lowering with statins after acute coronary syndromes. N Engl J Med 2004; 350:1495-504.
8. Cannon C P, McCabe C H, Belder R, Breen J, Braunwald E. Design of the Pravastatin or Atorvastatin Evaluation and Infection Therapy (PROVE IT)-TIMI 22 trial. Am J cardiol 2002; 89:860-1.
9. Nissen S E, Tuzcu E M, Schoenhagen P, et al. Effect of intensive compared with moderate lipid-lowering therapy on progression of coronary atherosclerosis. JAMA 2004; 291:1071-80.
10. Grundy S M, Cleeman J I, Noel Bairey Merz C, et al for the Coordinating Committee of the National Cholesterol Education Program. Implications of recent clinical trials for the National Cholesterol Education Program Adult treatment Panel III guidelines. Circulation 2004; 110:227-239.
11. Ridker P M, Cushman M, Stampfer M J, Tracy R P, Hennekens C H. Inflammation, aspirin, and the risk of cardiovascular disease in apparently healthy men. N Engl J Med 1997; 336:973-9.
12. Ridker P M, Rifai N, Rose L, Buring J E, Cook N R. Comparison of C-reactive protein and low-density lipoprotein cholesterol levels in the prediction of first cardiovascular events. N Engl J Med 2002; 347:1557-65.
13. Koenig W, Lowel H, Baumert J, Meisinger C. C-reactive protein modulates risk prediction based on the Framingham Score: implications for future risk assessment: results from a large cohort study in southern Germany. Circulation 2004; 109:1349-53.
14. Ballantyne C M, Hoogeveen R C, Bang H, et al. Lipoprotein-associated phospholipase A2, high-sensitivity C-reactive protein, and risk for incident coronary heart disease in middle-aged men and women in the Atherosclerosis Risk in Communities (ARIC) study. Circulation 2004; 109:837-42.
15. Danesh J, Wheeler J G, Hirschfield G M, et al. C-reactive protein and other circulating markers of inflammation in the prediction of coronary heart disease. N Engl J Med 2004; 350:1387-97.
16. Ridker P M, Cook N. Clinical usefulness of very high and very low levels of C-reactive protein across the full range of Framingham Risk Scores. Circulation 2004; 109:1955-9.
17. Liuzzo G, Biasucci L M, Gallimore J R, et al. The prognostic value of C-reactive protein and serum amyloid A protein in severe unstable angina. N Engl J Med 1994; 331:417-24.
18. Haverkate F, Thompson S G, Pyke S D, Gallimore J R, Pepys M B. Production of C-reactive protein and risk of coronary events in stable and unstable angina. European Concerted Action on Thrombosis and Disabilities Angina Pectoris Study Group. Lancet 1997; 349:462-6
19. Lindahl B, Toss H, Siegbahn A, Venge P, Wallentin L. Markers of myocardial damage and inflammation in relation to long-term mortality in unstable coronary artery disease. FRISC Study Group. Fragmin during Instability in Coronary Artery Disease. N Engl J Med 2000; 343:1139-47.
20. Morrow D A, Rifai N, Antman E M et al. C-reactive protein is a potent predictor of mortality independently of and in combination with troponin T in acute coronary syndromes: a TIMI 11A substudy. J Am Coll Cardiol 1998; 31:1460-5.
21. Kinlay S, Timms T, Clark M, et al. Comparison of effect of intensive lipid lowering with atorvastatin to less intensive lowering with lovastatin on C-reactive protein in patients with stable angina pectoris and inducible myocardial ischemia. Am J Cardiol 2002; 89:1205-7.
22. Jialal I, Stein D, Balis D, et al. Effect of hydroxymethyl glutaryl coenzyme A reductase inhibitor therapy on high sensitive C-reactive protein levels. Circulation 2001; 103:1933-5.
23. Libby P. Inflammation in atherosclerosis. Nature 2002; 420:868-74
24. Davignon J. Beneficial cardiovascular pleiotropic effects of statins. Circulation 2004; 109[suppl III]:III-39-III-43.
25. Kinlay S, Schwartz G G, Olsson A G, et al. High-dose atorvastatin enhances the decline in inflammatory markers in patients with acute coronary syndromes in the MIRACL study. Circulation 2003; 108:1560-6.
26. Ridker P M, Wilson P W F, Grundy S M. Should C-reactive protein be added to metabolic syndrome and to assessment of global cardiovascular risk? Circulation 2004; 109:2818-2825.
27. Ridker P M. Rosuvastatin in the primary prevention of cardiovascular disease among patients with low levels of low-density lipoprotein cholesterol and elevated high-sensitivity C-reactive protein: rationale and design of the JUPITER trial. Circulation 2003; 108:2292-7.

I claim:

1. A method for diagnosing a human subject, comprising:
   (i) obtaining a level of C-reactive protein (CRP) in a human subject who has been diagnosed and who is in a course of treatment with a statin to reduce the risk of a future cardiovascular event,
   (ii) comparing the level of CRP obtained in (i) to a predetermined value corresponding to a level of CRP in an apparently healthy control population, and
   (iii) changing therapy when the level of CRP obtained in (i) is above the predetermined value.

2. The method of claim 1, wherein step (i) is repeated so as to monitor the human subject's levels of CRP over time.

3. The method of claim 2, wherein the human subject has been undergoing the therapy for at least one month.

4. The method of claim 2, wherein the human subject has been undergoing the therapy for at least two months.

5. The method of claim 1, wherein the human subject has been undergoing the therapy for at least one month.

6. The method of claim 1, wherein the human subject has been undergoing the therapy for at least two months.

7. The method of claim 1, wherein the predetermined value is about 1 mg/L or higher.

8. The method of claim 1, wherein the predetermined value is about 1.25 mg/L or higher.

9. The method of claim 1, wherein the predetermined value is about 1.5 mg/L or higher.

10. The method of claim 1, wherein the predetermined value is about 1.75 mg/L or higher.

11. The method of claim 1, wherein the predetermined value is about 2 mg/L or higher.

12. A method for evaluating the efficacy of a therapy for reducing the risk of a future cardiovascular event comprising:
    (i) obtaining a level of C-reactive protein (CRP) in a human subject who has been diagnosed and who is in a course of treatment with a statin to reduce the risk of a future cardiovascular event,
    (ii) comparing the level of the marker obtained in (i) to a predetermined value corresponding to a level of CRP in an apparently healthy control population, and
    (iii) identifying the therapy with a statin as not efficacious and changing therapy when the level of CRP obtained in (i) is above the predetermined value.

13. The method of claim 12, wherein the human subject has been undergoing the therapy for at least one month.

14. The method of claim 12, wherein the human subject has been undergoing the therapy for at least two months.

15. The method of claim 12, wherein step (i) is repeated so as to monitor the human subject's levels of CRP over time.

16. The method of claim 15, wherein the human subject has been undergoing the therapy for at least one month.

17. The method of claim 15, wherein the human subject has been undergoing the therapy for at least two months.

18. The method of claim 12, wherein the predetermined value is about 1 mg/L or higher.

19. The method of claim 12, wherein the predetermined value is about 1.25 mg/L or higher.

20. The method of claim 12, wherein the predetermined value is about 1.5 mg/L or higher.

21. The method of claim 12, wherein the predetermined value is about 1.75 mg/L or higher.

22. The method of claim 12, wherein the predetermined value is about 2 mg/L or higher.

23. A method for diagnosing a human subject, comprising:
    (i) performing an assay on a body fluid sample obtained from a human subject to obtain a level of C-reactive protein (CRP) in the human subject who has been diagnosed and who is in a course of treatment with a statin to reduce the risk of a future cardiovascular event,
    (ii) comparing the level of CRP obtained in (i) to a predetermined value corresponding to a level of CRP in an apparently healthy control population, and
    (iii) identifying the therapy with the statin as not efficacious and changing therapy when the level of CRP obtained in (i) is above the predetermined value.

24. The method of claim 23, wherein the predetermined value is about 1 mg/L or higher.

25. The method of claim 23, wherein the predetermined value is about 1.25 mg/L or higher.

26. The method of claim 23, wherein the predetermined value is about 1.5 mg/L or higher.

27. The method of claim 23, wherein the predetermined value is about 1.75 mg/L or higher.

28. The method of claim 23, wherein the predetermined value is about 2 mg/L or higher.

* * * * *